(12) United States Patent
Suarez (10) Patent No.: US 9,549,838 B2
(45) Date of Patent: Jan. 24, 2017

(54) MEDICAL DEVICE FOR ERECTILE DYSFUNCTION AND JOINT IMMOBILIZATION

(71) Applicant: Jose David Suarez, Miami, FL (US)

(72) Inventor: Jose David Suarez, Miami, FL (US)

(73) Assignee: Jose David Suarez

( * ) Notice: Subject to any disclaimer, the term of this patent is extended or adjusted under 35 U.S.C. 154(b) by 0 days.

(21) Appl. No.: 14/683,849

(22) Filed: Apr. 10, 2015

(65) Prior Publication Data

US 2016/0296362 A1    Oct. 13, 2016

(51) Int. Cl.
*A61F 5/41*    (2006.01)
*A61F 5/01*    (2006.01)

(52) U.S. Cl.
CPC .................. *A61F 5/41* (2013.01); *A61F 5/012* (2013.01); *A61F 2005/411* (2013.01); *A61F 2250/0003* (2013.01)

(58) Field of Classification Search
CPC ........ A61F 5/41; A61F 6/04; A61F 2005/414; A61F 2006/043; A61F 2006/048
USPC ........................................................ 600/38–41
See application file for complete search history.

(56) References Cited

U.S. PATENT DOCUMENTS

| 4,281,648 | A | * | 8/1981 | Rogers | ..................... | A61F 6/04 |
| | | | | | | 128/844 |
| 4,895,140 | A | * | 1/1990 | Bellak | ............................. | 600/39 |
| 5,622,186 | A | * | 4/1997 | Schwartz | ...................... | 128/842 |
| 5,885,205 | A | * | 3/1999 | Kassman | ........................ | 600/38 |
| 7,261,685 | B2 | * | 8/2007 | Wu | .................................. | 600/39 |
| 8,123,674 | B2 | * | 2/2012 | Kuyava | ............................ | 600/40 |

\* cited by examiner

*Primary Examiner* — Samuel Gilbert
(74) *Attorney, Agent, or Firm* — Christian Sanchelim (57) ABSTRACT

An erection-facilitating sleeve for counteracting the effects of erectile dysfunction. The erection-facilitating sleeve includes two open ends at each distal end spaced apart by a plurality of inflatable, semi-rigid passages that extend in a braided, or crisscross, configuration from the base to the top of the sleeve. The sleeve is inserted onto the penis and is made of a resilient material that wraps tightly around the sex organ of a user. The semi-rigid passages are of a predetermined material and thickness so that a user's sex organ maintains at least partially erect even while suffering from erectile dysfunction.

9 Claims, 11 Drawing Sheets

MEDICAL DEVICE FOR ERECTILE DYSFUNCTION AND JOINT IMMOBILIZATION

BACKGROUND OF THE INVENTION

1. Field of the Invention

The present invention relates to a medical device for a penis and, more particularly, to a semi-rigid sleeve used to maintain the penis in an erect position during sexual intercourse. Such is advantageous in relieving symptoms of mild to moderate erectile dysfunction.

2. Description of the Related Art

The male impotence or erectile dysfunction is a widespread problem. It is the persistent inability of a man to get an erection and to maintain it long enough for satisfying sexual intercourse. The erectile dysfunction occurs mainly in older men; approximately 30% of men in their forties and 67% of men in their seventies are affected. Present treatments comprise vacuum pumps, penis protheses, vascular surgery, and the use of vasodilatory medicaments.

Several designs for condoms have been designed in the past. None of them, however, include an erection-facilitating sleeve made of flexible material allowing for movement that enhances comfort and pleasure having a plurality of semi-rigid resilient members that can be inflated to a sufficient rigidness to support an erection. Optionally, the present invention can also be implemented with an exoskeleton having a predetermined tensile strength to support an erection.

Applicant believes that a related reference corresponds to U.S. Pat. No. 7,972,263 issued to Runyan, Donald. The Runyan reference discloses of a penis rigidity stabilizer using a plurality of rigid strips. However, it differs from the present invention because the present invention uses a sleeve having semi-rigid resilient members configured in a braided, or crisscross, longitudinal configuration that supports to a user's penis during sexual intercourse. Also, the semi-rigid resilient members can be hollow and filled with air or water using a valve and a syringe to enhance the support to a user's penis. Additionally, the Runyan reference does not teach or motivate one of ordinary skill in the art to include a prophylactic membrane to a resilient sleeve permitting unidirectional and bi-directional movement that increases stimulation and comfort to a user. Moreover, the Runyan reference does not disclose the use of a manual pump that can be used to fill the semi-rigid resilient members of the present invention with air or water.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an erection-facilitating sleeve that counteracts the symptoms of erectile dysfunction.

It is another object of this invention to provide such an erection-facilitating sleeve that is comfortable when applying, removing, and using during sexual intercourse.

It is still another object of the present invention to provide such an erection-facilitating sleeve that has a configuration of semi-rigid resilient members that allows effective support to a user's penis.

It is another object of the present invention to provide such an erection-facilitation sleeve that includes a valve that can inflate the semi-rigid resilient members to provide enhanced support to a user's penis.

It is still another object of the present invention to provide such an erection-facilitating sleeve that includes a membrane fused to the sleeve that acts as a prophylactic.

It is yet another object of this invention to provide such a medical device that is inexpensive to implement and maintain while retaining its effectiveness.

It is another object of the present invention to optionally include a manual pump instead of a valve and syringe to inflate the semi-rigid resilient members.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
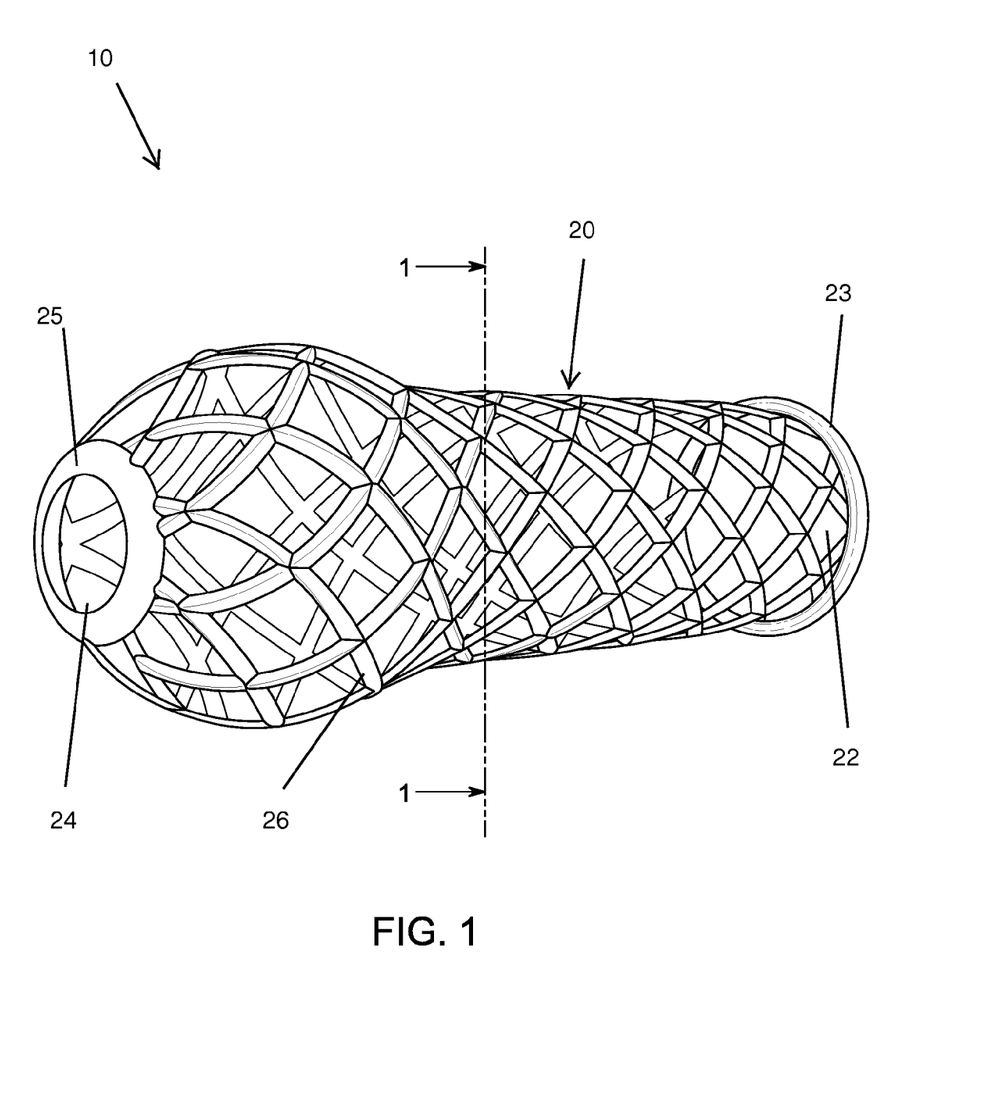
FIG. 1 represents an isometric view of erection-facilitating sleeve 20 having semi-rigid resilient members 26 extending in a braided, or crisscross, configuration from bottom resilient annular member 23 to top resilient annular member 25.
Figure 1A:
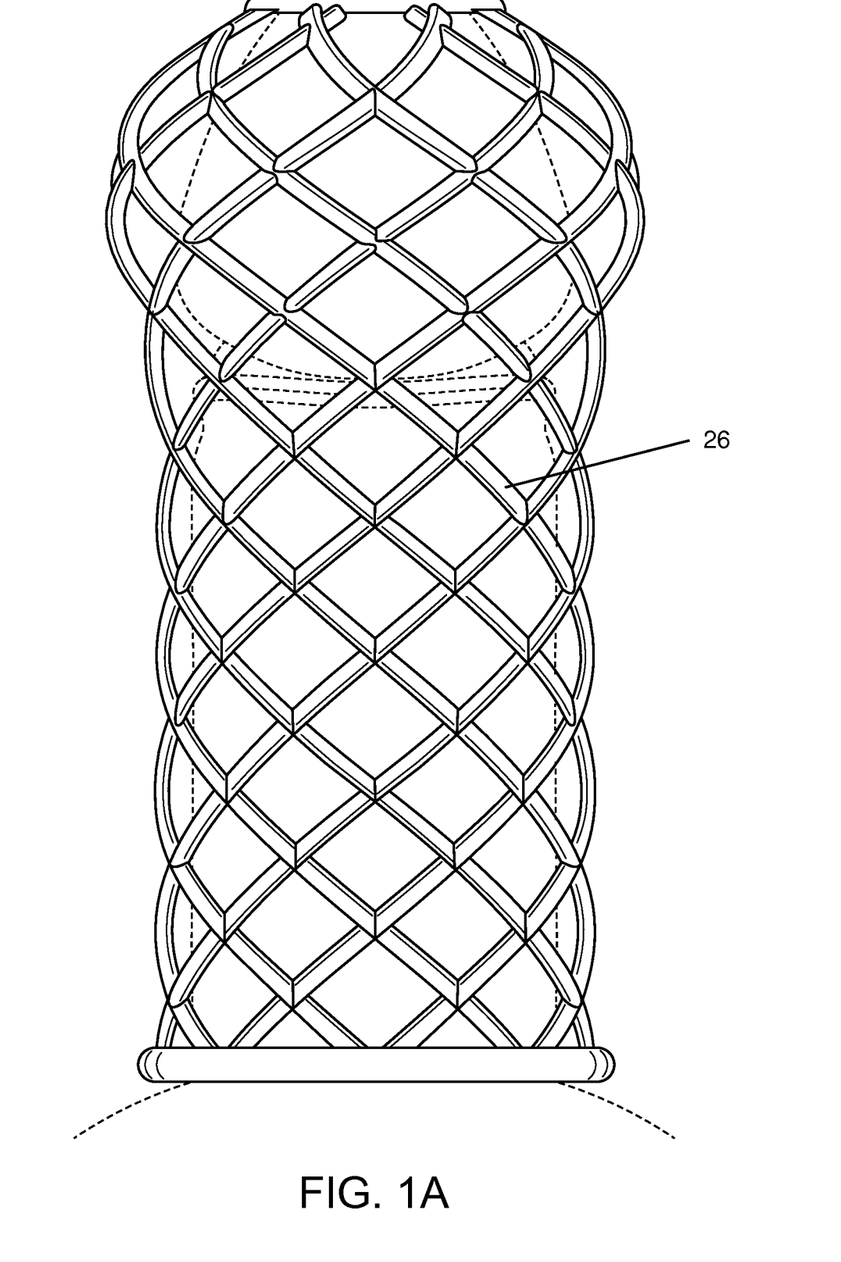
FIG. 1A is a side elevational view of erection-facilitating sleeve 20 further showing the braided configuration of semi-rigid resilient members 26.

Referring now to the drawings, where the present invention is generally referred to with numeral 10, it can be observed that it basically includes erection-facilitating sleeve assembly 20. As shown in FIGS. 1 and 1A, erection-facilitating sleeve assembly 20 includes bottom open end 22 and top open end 24 at its distal ends. Bottom open end 22 and top open end 24 are defined by bottom resilient annular member 23 and top resilient annular member 25, respectively.

As also seen in FIGS. 1 and 1A, bottom open end 22 and top open end 24 are spaced apart by a plurality of semi-rigid resilient members 26 that extend in a braided, or crisscross, configuration from bottom resilient annular member 23 to top resilient annular member 25.

Erection-facilitating sleeve assembly 20 is made of a resilient material that stretches and compresses to cooperate with the application onto a user's sex organ. In a preferred embodiment, erection-facilitating sleeve 20 is made of a non-allergenic, thin material with a high tensile strength, such as polyethylene. Other materials such as rubber, polyutherane, latex, AT-10 resin, silicone, and neoprene can also be comfortably used with the present invention.

Erection-facilitating sleeve 20 is inserted onto the penis and is made of a resilient material that wraps tightly around the sex organ of a user. Semi-rigid resilient members 26 are of a predetermined material and thickness so that a user's sex organ is at least partially erect even while suffering from erectile dysfunction.

Bottom resilient annular member 23 and top resilient annular member 25 are made of the same material as the rest of erection-facilitating sleeve assembly 20, in a preferred embodiment. Semi-rigid resilient members 26 extend from bottom open end 22 in a braided, or crisscross configuration, longitudinally along erection-facilitating sleeve assembly 20. Semi-rigid resilient members 26 are made of the same material as the rest of erection-facilitating sleeve assembly 20, in a preferred embodiment.

In an alternate embodiment, semi-rigid members 26 have a preselected flexibility and tensile strength that allows erection-facilitating sleeve assembly 20 to have uni-directional and bi-directional movement. Uni-directional and bi-directional permit a user to feel forward/back and side-to-side movement, respectively. This is to enhance pleasure to the user by allowing more comfortable movements during sexual intercourse as well as stimulating friction to the user's sexual organ.

Semi-rigid resilient members 26 extend in a longitudinal and braided configuration until reaching top open end 24 top resilient annular member 25 as seen in FIGS. 1-1A.

Figure 2:
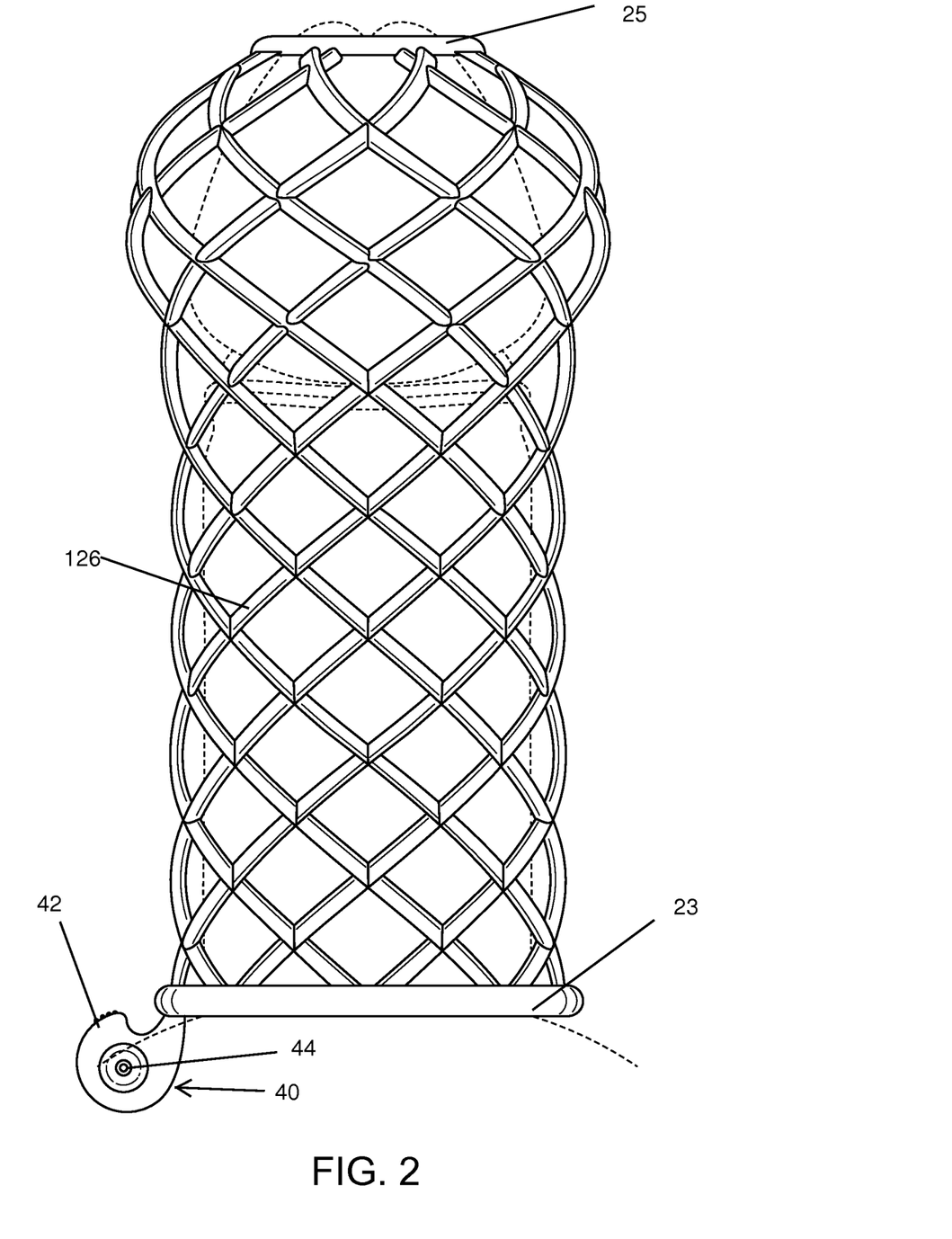
FIG. 2 shows a side elevational view of an alternate embodiment wherein valve 42 of valve assembly 40 has been mounted to semi-rigid resilient members 26 and bottom resilient annular member 83 of erection-facilitating sleeve 20.
Figure 2A:
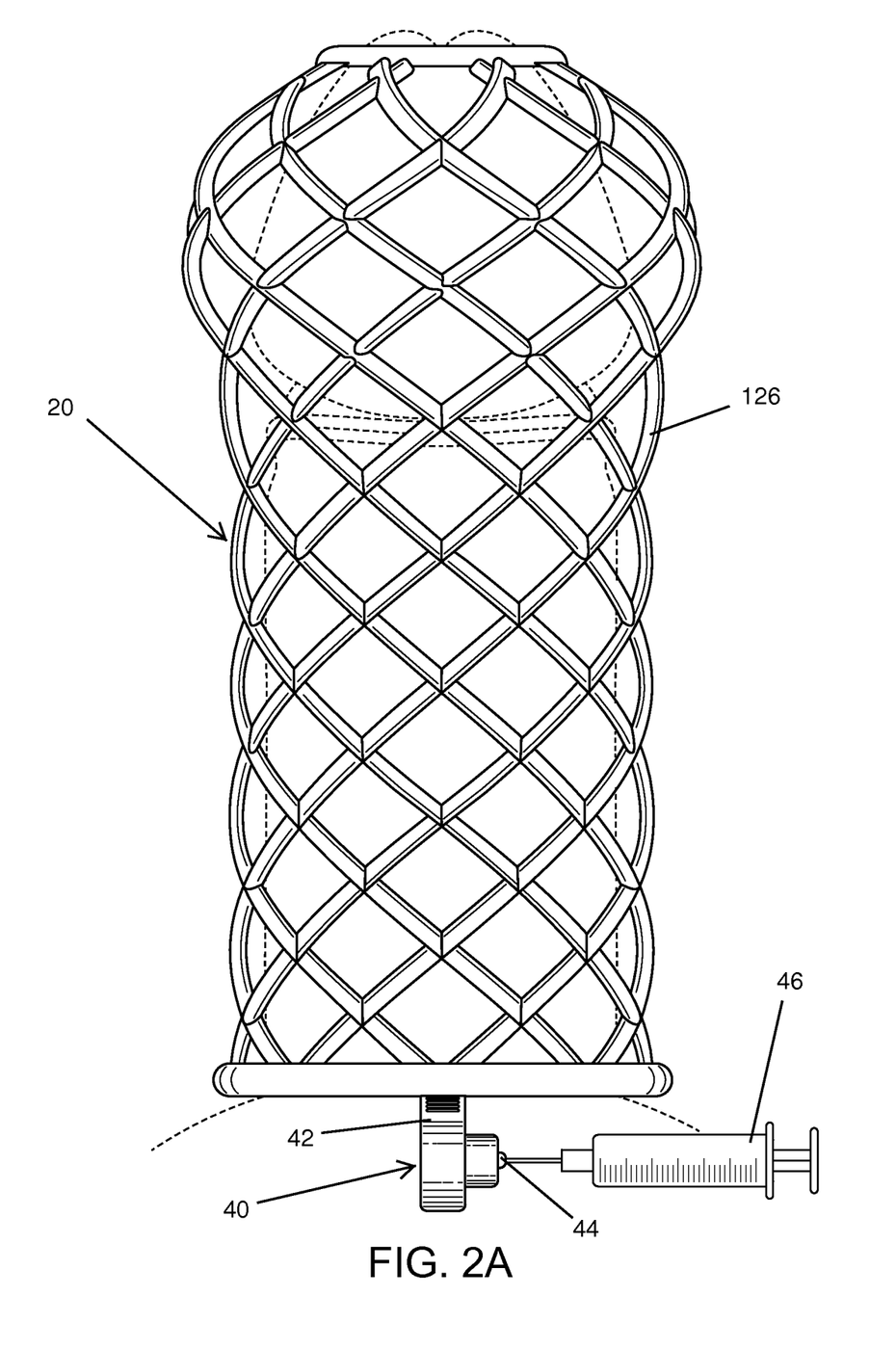
FIG. 2A illustrates a side elevational view of an alternate embodiment wherein syringe 46 can be seen in cooperating with valve 42 of valve assembly 40 to inject a liquid or gas, and thereby inflating, semi-rigid members 26 until a user achieves the desired sexual organ support.
Figure 2B:
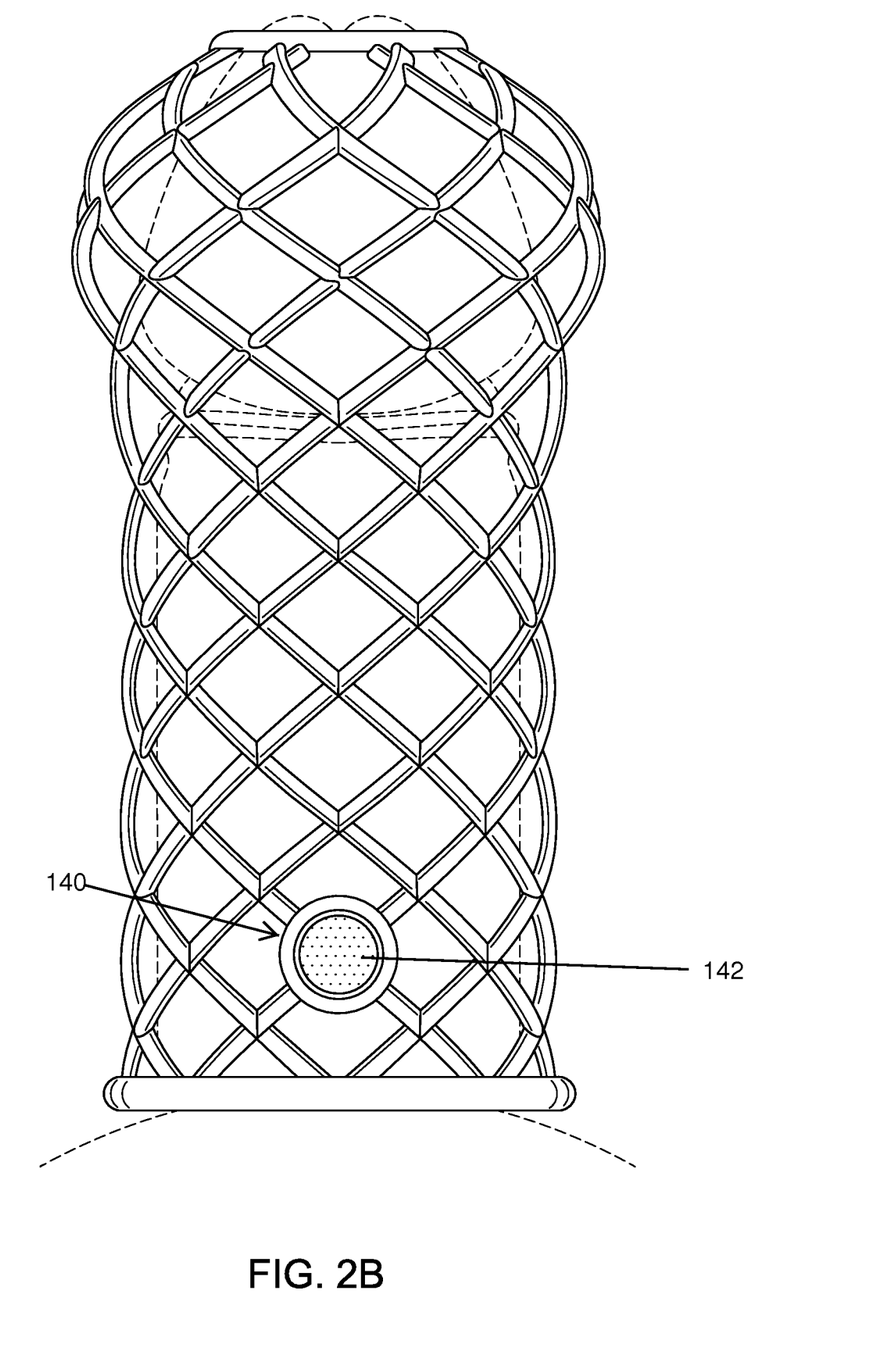
FIG. 2B shows a side elevational view of an alternate embodiment, wherein push pump assembly, 140 having pump 142 is seen mounted to semi-rig resilient members 26.
Figure 3:
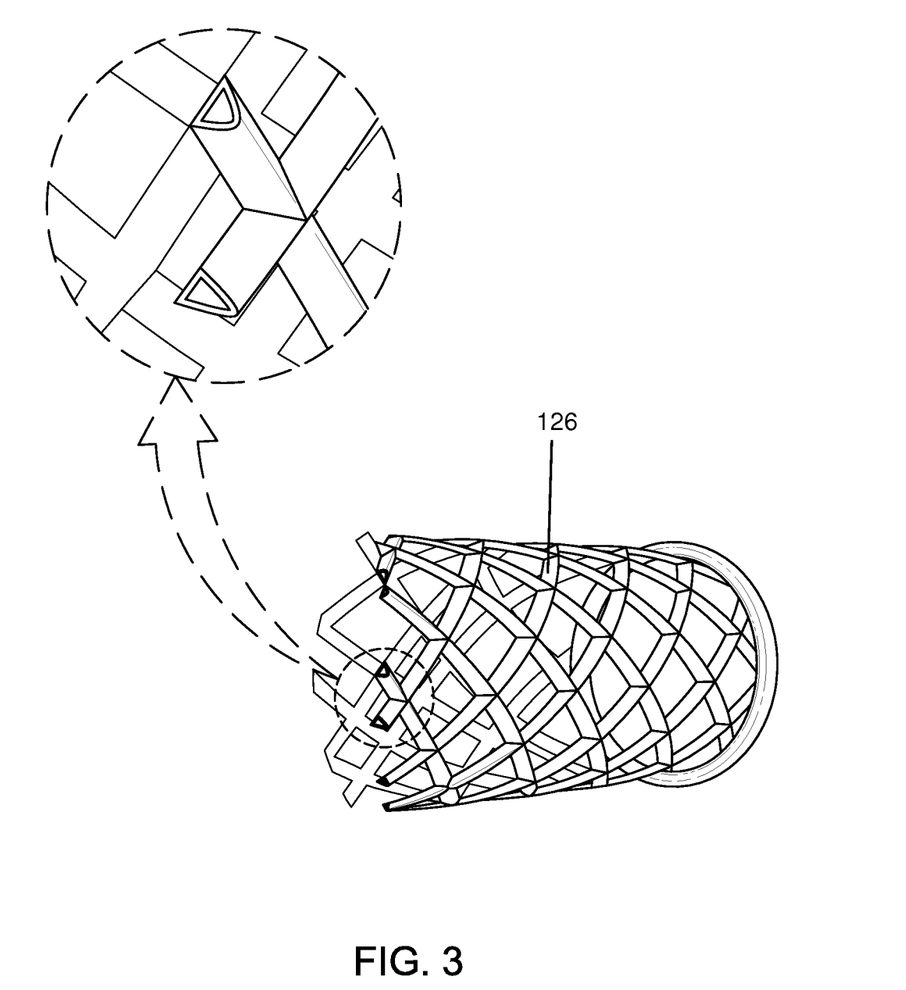
FIG. 3 is a representation of cross-section of an alternate embodiment along line 1-1 of FIG. 1 wherein semi-rigid resilient members 26 can be hollowed out to be able to receive a liquid or gas, these semi-rigid resilient members 26 can also be referred to as interconnected hollowed resilient members.

In an alternate embodiment, shown in FIGS. 2 and 2A valve assembly 40 can be mounted to hollowed semi-rigid resilient members 126 of erection-facilitating sleeve assembly 20. Valve assembly 40 includes valve 42 having valve opening 44 that can cooperate with syringe 46, as shown in FIG. 2A, to fill hollowed semi-rigid resilient members 126 with a gas or liquid, such as air and gas, respectively. Syringe 46 can include a Luer lock to provide a more secure application of the gas or liquid. The gas or liquid is injected into valve opening 44 then passes through the network of hollowed semi-rigid resilient members 126 until the desired penis support is achieved. Valve assembly 40 can be mounted at a predetermined location so it can serve as a clitoral stimulator to the person the user is having sexual intercourse with as shown in FIG. 2. Optionally, manual valve assembly 140 can use pump 142 instead of valve 42 so that a user can manually inflate hollowed semi-rigid resilient members 126 without requiring the use of syringe 46. The hallowed portions of hollowed semi-rigid resilient members 126 wherein gas or liquid is passed to inflate erection-facilitating sleeve assembly 20 is seen in FIG. 3.

Figure 4:
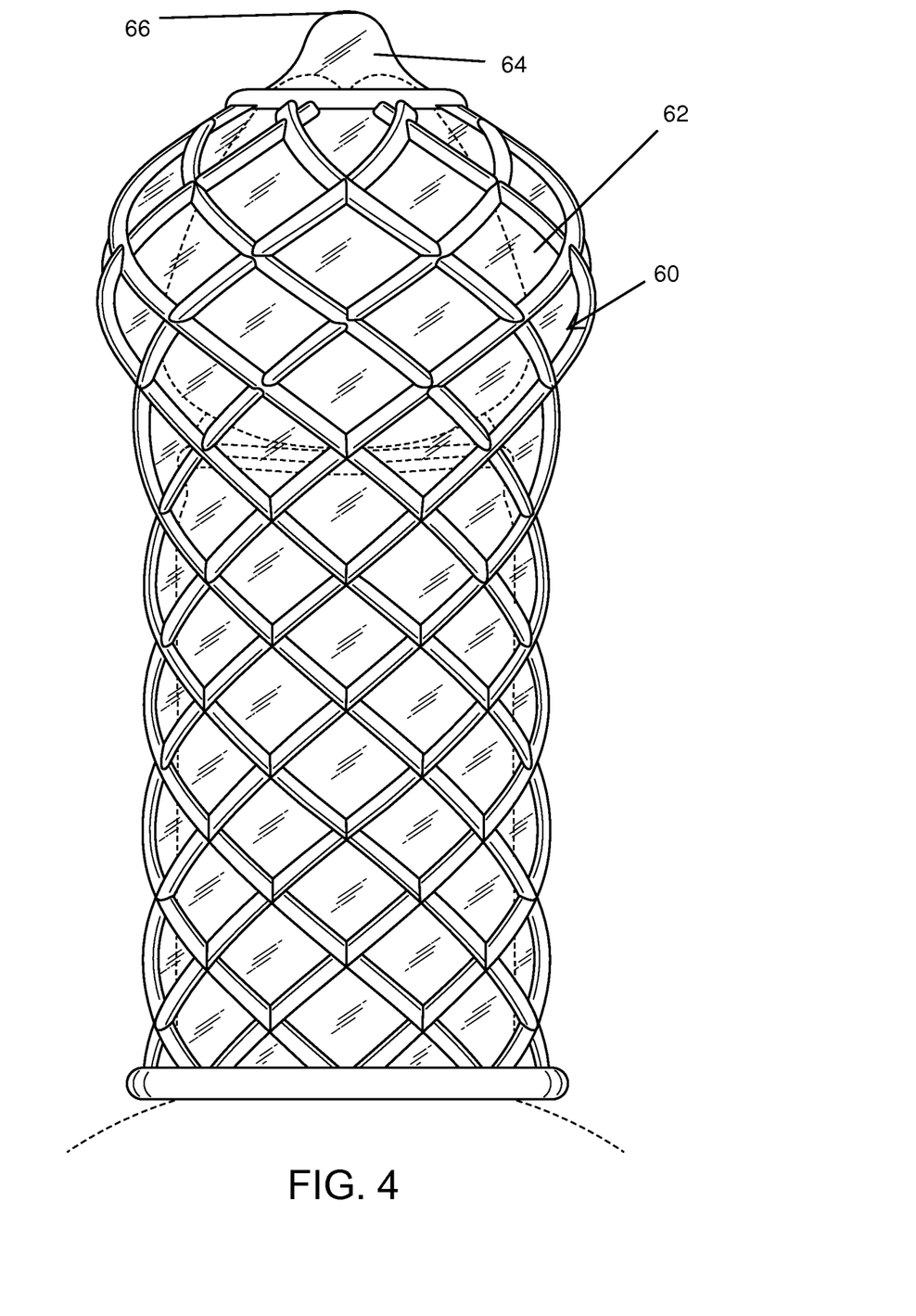
FIG. 4 is a side elevational view of another alternate embodiment wherein membrane assembly 60 is mounted to sleeve 20 to serve as a prophylactic. Semi-rigid resilient members 26 can be seen embedded to but extending out from membrane assembly 60 in an exophytic configuration.
Figure 4A:
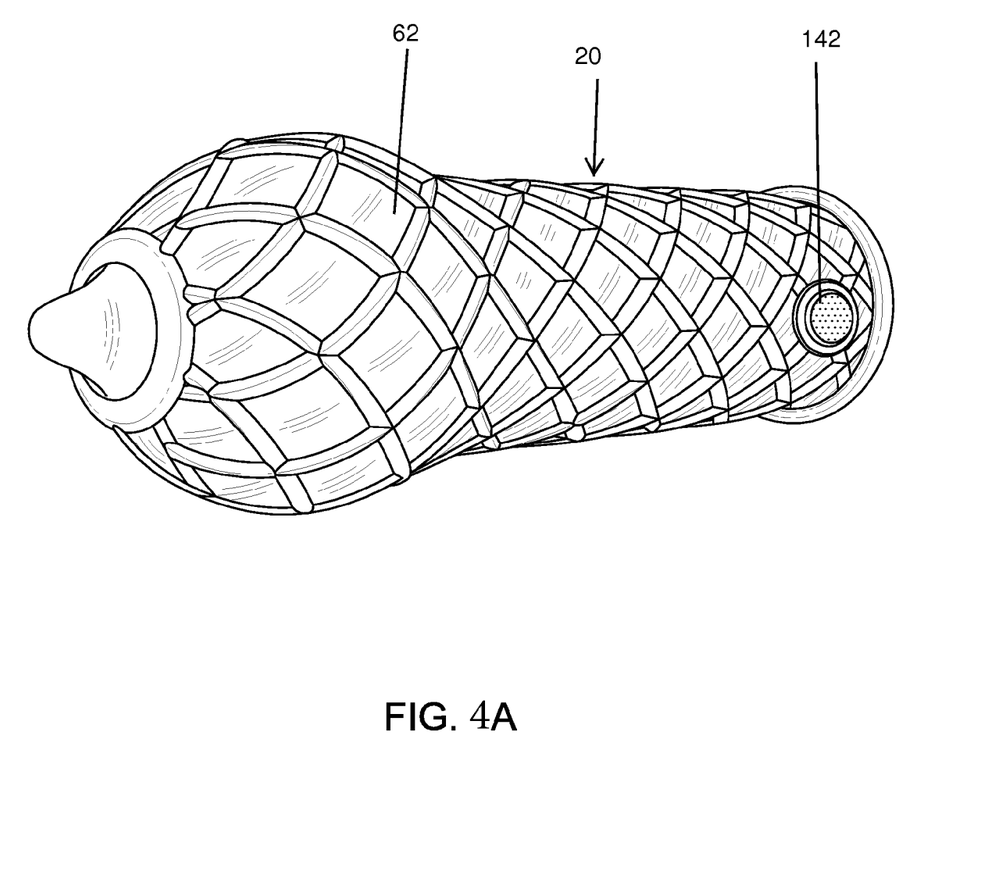
FIG. 4A is an isometric view of the alternate embodiment subject of FIG. 5 wherein the exophytic configuration between semi-rigid resilient members 26 and membrane assembly 60 can be further seen. Also, pump 142 can be seen mounted to semi-rigid resilient members 26.

In an alternate embodiment, shown in FIGS. 4 and 4A, erection-facilitating sleeve assembly 20 can be seen embedded with membrane assembly 60 having membrane 62, semen reservoir 64, and tip 66. Membrane 62 is tailored to run along the entire interior of erection-facilitating sleeve 20 while still maintaining an interior cavity within erection-facilitating assembly 20 permitting the insertion of a penis. Semen reservoir 64 flares outwardly beginning at approximately the base of the glans and tapers inwardly at the top of the glans thereby creating a dome-like shape around the glans to serve as a semen reservoir.

Tip 66 extends from the top distal end of membrane 62 and defines the distalmost portion of semen reservoir 64 which receives semen upon a user ejaculating, thus, preventing semen from leaking out of the bottom of erection-facilitating sleeve assembly 20. Membrane 62, in a preferred embodiment, is made of the same material, erection-facilitating assembly 20, although thinner. Membrane 62 is embedded to the inside of erection-facilitating assembly 20 so that semi-rigid resilient members 26 become an exophytic skeleton for membrane 62. An alternate embodiment is shown in FIG. 4A wherein erection-facilitating sleeve assembly 20 has been embedded with membrane 62 and pump 142 is mounted to hollowed semi-rigid resilient members 126 to allow a user to manually inflate erection-facilitating sleeve assembly 20 to a desired level of support.

Figure 5:
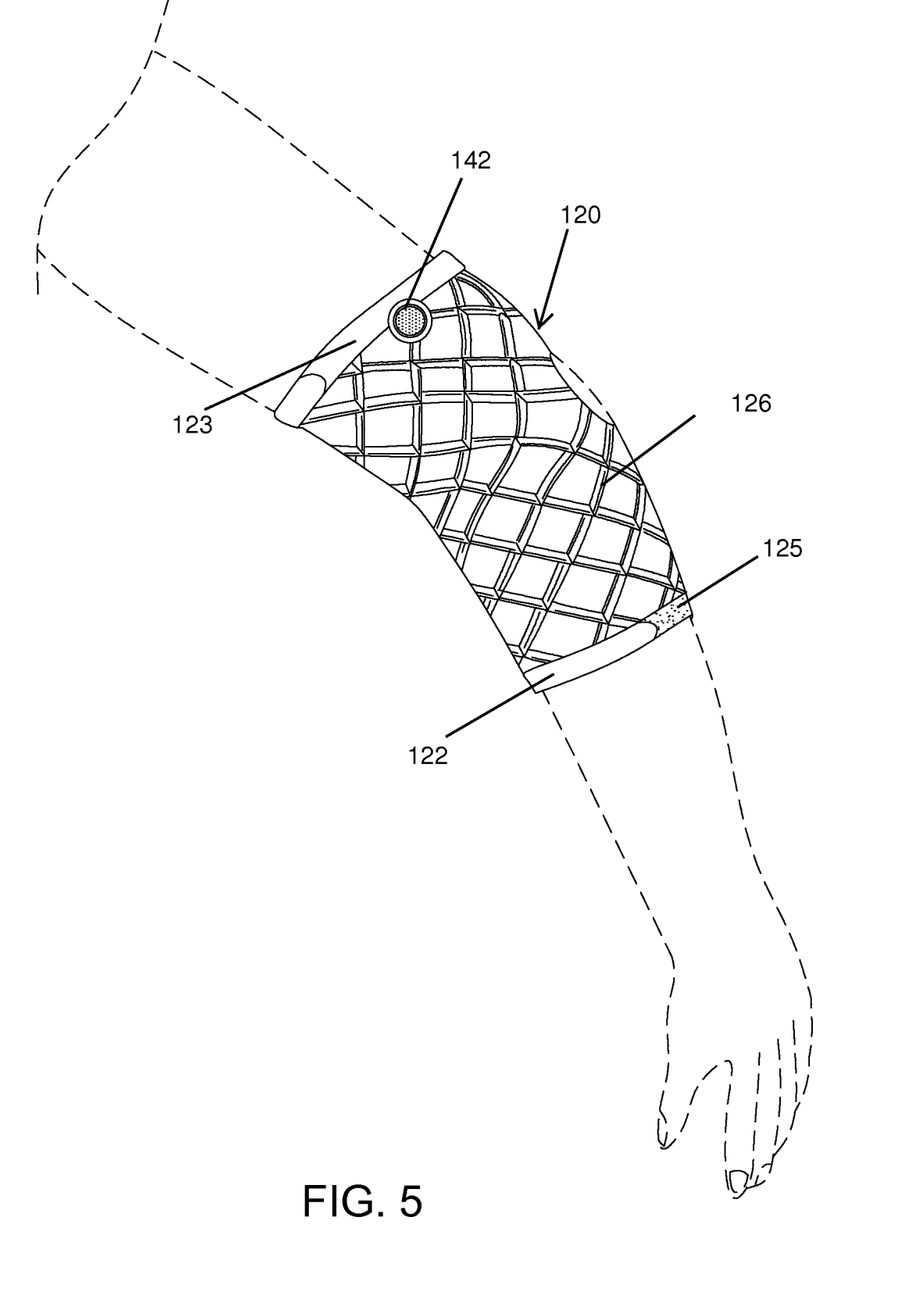
FIG. 5 shows an alternate embodiment of the present invention where it has been adapted to cooperate with the elbow of a user. Semi-resilient members 26 are still used to assist in immobilizing the area and pump 142 is seen that used to inflate semi-rigid resilient members 26.

As seen in FIG. 5, an alternate embodiment is shown wherein elbow-immobilizing sleeve assembly 120 is used to assist in the immobilization of a user's elbow. Immobilizing sleeve assembly 120 includes top annular member 123 and bottom annular member 125 that define the upper and lower distal ends of immobilizing sleeve assembly 120. Optionally, strap 122 can be used to secure top and bottom annular members 123; 125, respectively, to a user's elbow. Immobilizing sleeve assembly 120 also includes hollowed semi-rigid resilient members 126 that can be manually inflated to a user selected level of immobilization using pump 142.

Figure 6:
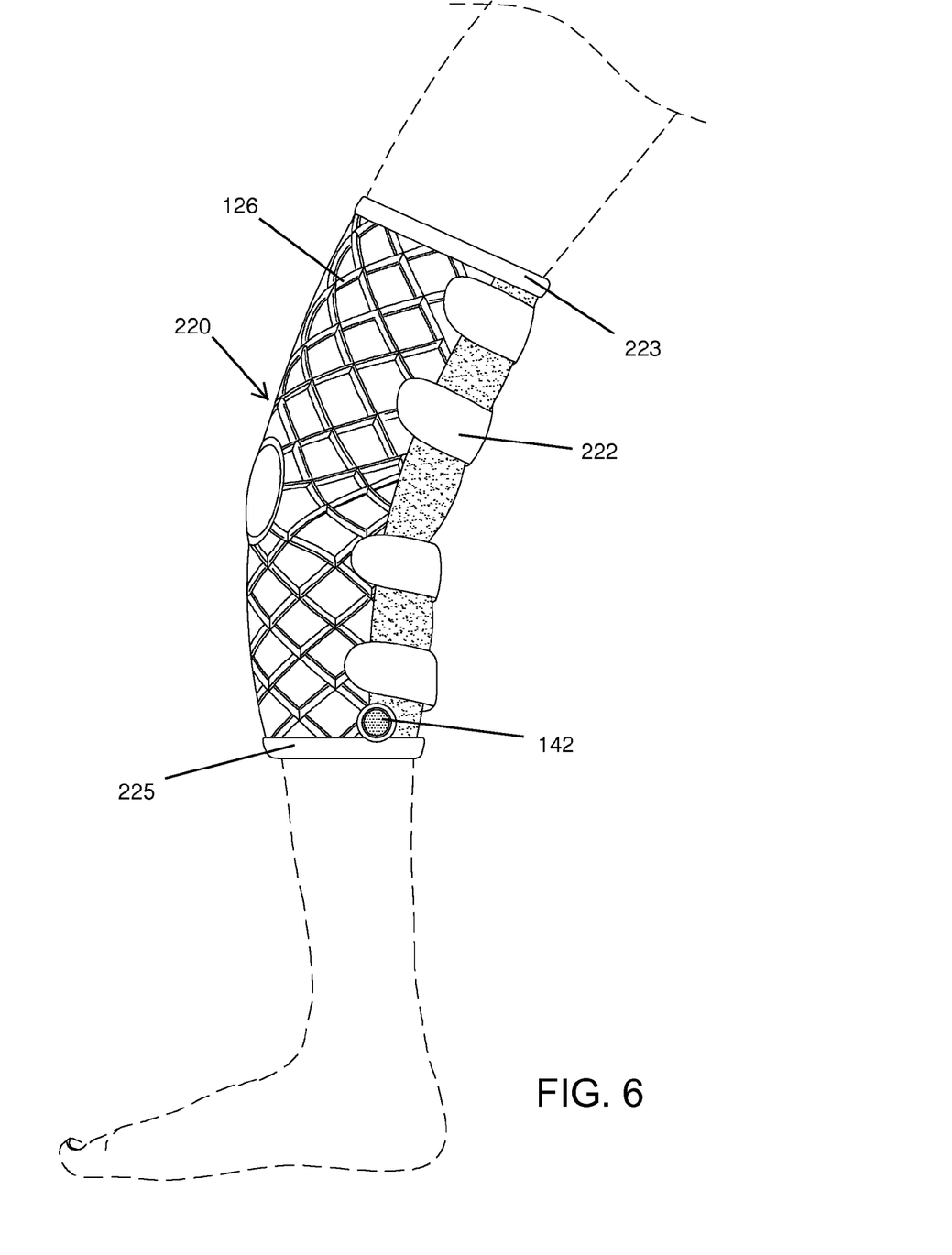
FIG. 6 shows an alternate embodiment of the present invention where it has been adapted to cooperate with the knee of a user. Semi-resilient members 26 are still used to assist in immobilizing the area and pump 142 is seen that used to inflate semi-rigid resilient members 26. Furthermore, straps 100 are used to cooperatively mount the embodiment around the knee of the user.

As seen in FIG. 6, an alternate embodiment is shown wherein knee-immobilizing sleeve assembly 220 is used to assist in the immobilization of a user's knee Immobilizing sleeve assembly 220 includes top annular member 223 and bottom annular member 225 that define the upper and lower distal ends of immobilizing sleeve assembly 120. Optionally, strap 222 can be used to secure top and bottom annular members 223; 225, respectively, to a user's knee. Immobilizing sleeve assembly 220 also includes hollowed semi-rigid resilient members 126 that can be manually inflated to a user-selected level of immobilization using pump 142.

Figure 7:
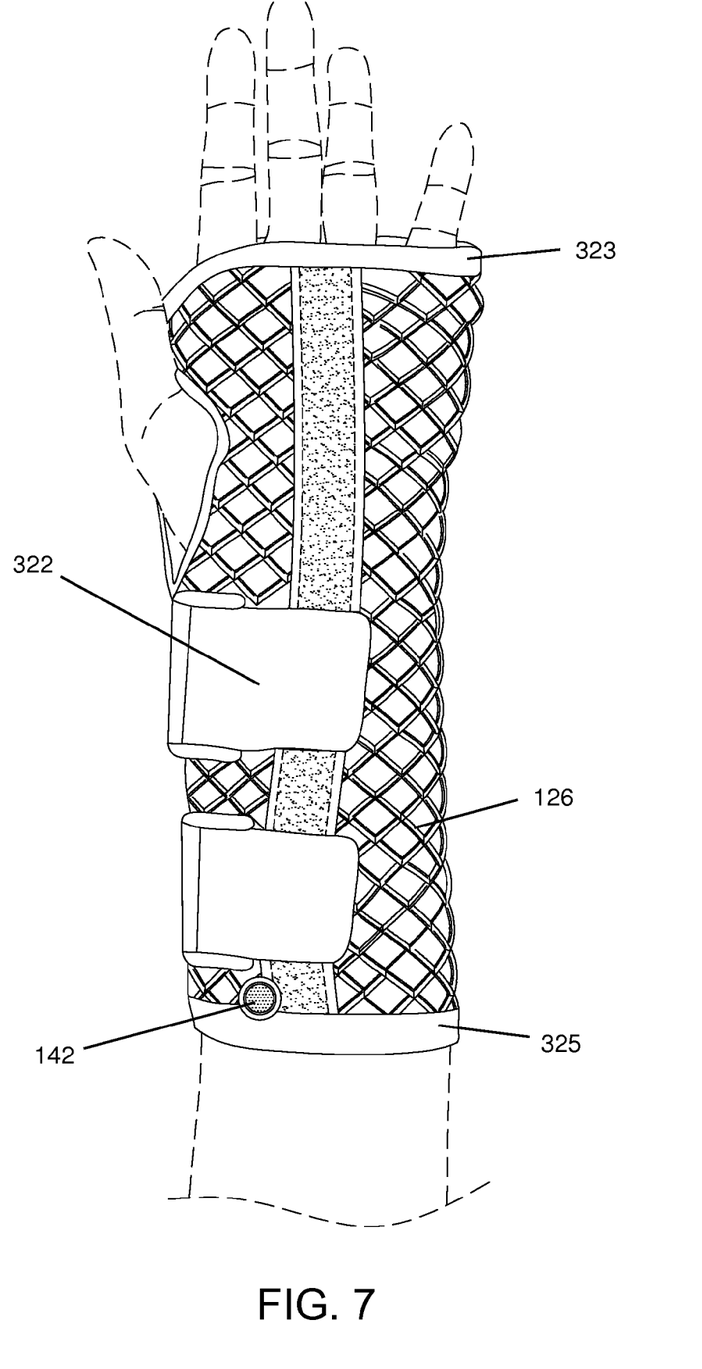
FIG. 7 shows an alternate embodiment of the present invention where it has been adapted to cooperate with the wrist of a user. Semi-resilient members 26 are still used to assist in immobilizing the area and pump 142 is seen that used to inflate semi-rigid resilient members 26. Furthermore, straps 200 are used to cooperatively mount the embodiment around the knee of the user.

As seen in FIG. 7, an alternate embodiment is shown wherein wrist-immobilizing sleeve assembly 320 is used to assist in the immobilization of a user's wrist. Immobilizing sleeve assembly 320 includes top annular member 323 and bottom annular member 325 that define the upper and lower distal ends of immobilizing sleeve assembly 320. Optionally, strap 322 can be used to secure top and bottom annular members 323; 325, respectively, to a user's wrist. Immobilizing sleeve assembly 320 also includes hollowed semi-rigid resilient members 126 that can be manually inflated to a user-selected level of immobilization using pump 142.

In all three alternate embodiments shown in FIGS. 5-7, elbow immobilizing sleeve assembly 120, knee immobilizing sleeve assembly 220, and wrist-immobilizing sleeve assembly 320 can be covered by a solid sleeve covering to prevent fingers from being caught in between the semi-rigid members.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An erection-facilitating sleeve made of a resilient material that is adapted to receive a penis, said sleeve having a bottom end defined by a bottom resilient annular member and a top end defined by a top resilient annular member, said sleeve further including inter-connected, hollowed resilient members having an exterior surface and an interior, said inter-connected, hollowed resilient members extending in a braided configuration from said bottom resilient annular member to said top resilient annular member, said inter-connected, hollowed resilient members allowing air flow between each other at predetermined crossing points of their braided configurations, an inflating assembly mounted to the exterior surface of said inter-connected, hollowed resilient members adjacent to the said bottom end, said inflating assembly having a bottom side that includes an opening that connects with said hollowed semi-rigid resilient members.

2. The erection-facilitating sleeve in claim 1 wherein a membrane is embedded to the interior of said inter-connected, hollowed resilient members, said inter-connected, hollowed resilient members cooperate when mounted with said membrane to become an exophytic skeleton extending outwardly from said membrane, said membrane having a semen reservoir at its top distal end.

3. The erection-facilitating sleeve in claim 2 wherein said inflating assembly has a top side defined by a pump.

4. The erection-facilitating sleeve in claim 1 wherein said inflating assembly includes a valve mounted to said hollowed inter-connected, hollowed resilient members at a preselected location adjacent to said bottom end, said valve having first and second faces opposite each other, said first face having a first opening connected to said inter-connected, hollowed members, said second face having a second opening to cooperate with a syringe, said syringe removably connected to said erection-facilitating sleeve and said syringe injecting gas or liquid into said second opening on said second face.

5. The erection-facilitating sleeve in claim 4 wherein said inflating assembly is mounted to said inter-connected, hollowed resilient members at the preselected location adjacent to said bottom end, thereby adapted to stimulate a partner's clitoris.

6. The erection-facilitating sleeve in claim 4 wherein said syringe is a Luer lock syringe.

7. The erection-facilitating sleeve in claim 1 wherein said inter-connected, hollowed resilient members have a predetermined flexibility and tensile strength to allow for uni-directional and bi-directional movement during sexual intercourse.

8. The erection-facilitating sleeve in claim 7 wherein said inflating assembly has a top side defined by a pump.

9. The erection-facilitating sleeve in claim 1 wherein said inflating assembly has a top side defined by a pump.

\* \* \* \* \*